United States Patent [19]

Calbick et al.

[11] Patent Number: 5,274,149
[45] Date of Patent: Dec. 28, 1993

[54] PROCESS FOR MAKING ALKYL ARSINE COMPOUNDS

[75] Inventors: C. Joseph Calbick, Weston, Conn.; Mark A. Kuck, Upper Montclair, N.J.; Donald H. Valentine, Ridgefield, Conn.

[73] Assignee: American Cyanamid Company, Stamford, Conn.

[21] Appl. No.: 848,505

[22] Filed: Mar. 9, 1992

Related U.S. Application Data

[63] Continuation-in-part of Ser. No. 728,501, Jul. 11, 1991, abandoned.

[51] Int. Cl.⁵ .............................................. C07F 9/72
[52] U.S. Cl. ....................................... 556/70; 437/104; 437/107; 437/133
[58] Field of Search .................. 556/69, 70; 437/104, 437/107, 126, 133

[56] References Cited

U.S. PATENT DOCUMENTS

| | | | |
|---|---|---|---|
| 4,368,098 | 1/1983 | Manasevit | 156/612 |
| 4,404,265 | 9/1983 | Manasevit | 156/612 |
| 4,734,514 | 3/1988 | Melas et al. | 556/70 |
| 4,857,655 | 8/1989 | Valentine, Jr. | 556/70 |
| 5,003,093 | 3/1991 | Valentine, Jr. | 556/70 |
| 5,068,372 | 11/1991 | Kanjolia et al. | 556/70 |

Primary Examiner—Olik Chaudhuri
Assistant Examiner—Ourmazd S. Ojan

[57] ABSTRACT

Alkyl arsines are made by a reaction of gaseous arsine and the corresponding gaseous olefin in contact with at least one Bronsted acid catalyst. Products produced thereby are mono- and di-substituted arsines, e.g. alkyl and di-alkyl arsines, which contain substantially no metallic or oxygenating impurities.

7 Claims, 2 Drawing Sheets

PROCESS FOR MAKING ALKYL ARSINE COMPOUNDS

This application is a continuation-in-part of U.S. application Ser. No. 07/728,501, filed Jul. 11, 1991, now abandoned.

BACKGROUND OF THE INVENTION

The manufacture of semiconductor devices such as solar cells and computer chips is conducted through processes such as metalorganic chemical vapor deposition (MOCVD) wherein volatile sources of arsenic are useful as reactants therein. Such sources of arsenic must further be of high quality for use in such applications. Arsine has typically served as the volatile arsenic source. Use of arsine is undesirable because it is difficult to purify and especially because it is used as a compressed gas under elevated pressure, with resulting safety and environmental hazards due to the high toxicity of arsine and its persistence in the atmosphere. In recent years, alkylarsines, and especially mono-tertiary-butylarsine, have gained acceptance as replacements for arsine, due to their lower toxicity and presence in the liquid state under normal storage and handling conditions. Mono-arsines for use in semiconductor applications must be of high chemical purity, containing minimum amounts of stereoisomers or other chemical compounds and, especially, substantially no metallic or oxygenating impurities. Use of such very high purity mono-alkylarsines makes possible the fabrication of high quality semiconductor materials with properties equal or superior to materials made using arsine gas, but without the health and environmental hazards associated with use thereof. Therefore, a process is needed to make very high purity mono-arsines, containing virtually no metallic or oxygenating impurities.

One method to produce alkylarsines involves a Grignard reaction with arsenic trichloride to produce an alkylated arsenic chloride derivative, which is converted to the alkylated arsenic hydride (alkylarsine) by treatment with $LiAlH_4$, $NaBH_4$, $Zn/HCl$, or the like. Mono-tertiary-butylarsine was prepared by Tzschach et al. Z. anorg. allgem. Chem. 336, 36 (1965), using the above method. It has been found that mono-tertiary-butylarsine prepared by the above method contains characteristic germanium and other donor impurities, derived from the many reagents and solvents used, which are incompatible with growth of high quality semiconductors.

An alternative route to alkylarsines, disclosed for example in U.S. Pat. No. 5,068,372, is the reaction of an alkyl iodide and sodium arsenite to give an arsenious acid, $(alkyl)As(OH)_2$, which can be converted to the corresponding $(alkyl)AsH_2$, by treatment with $LiAlH_4$, $NaBH_4$, $Zn/HCl$, or the like. This method is, however, limited to the use of primary and a few secondary alkyl iodides, and cannot be used to prepare mono-tertiary-butylarsine.

Alternatively, the appropriate olefin may be reacted with the arsine in the liquid phase containing a liquid (U.S. Pat. No. 4,857,655) or solid acid catalyst (U.S. Pat. No. 5,003,093). These processes can be used to make high purity mono-tertiary-butylarsine. However, because of facile formation of di-tertiary-butylarsine in condensed phase reactions, it is necessary to use high arsine pressures (400 psi) and excess arsine, which it is difficult to recover and recycle. Even when high arsine pressures are used, the highest obtained mono-/di-tertiary-butyl arsine ratios are only approx. 3/1. Formation of the unwanted di-tertiary-butylarsine lowers yields of the desired mono-tertiary-butylarsine. Acid catalyzed formation of mono-tertiary-butylarsine in condensed phase thus involves extreme safety hazards due to use of compressed arsine, and severe disposal problems due to formation of other organoarsine products in addition to mono-tertiary-butylarsine and to the need to dispose of large quantities of aqueous acid wastes containing arsenated species.

It is therefore an object of the present invention to provide a process which is highly selective for the desired alkylarsine, and in particular, for mono-tertiary-butylarsine, and produces a high yield of product of relatively high quality, thereby obviating the necessity of costly purification procedures. It is a further object of the present invention to provide a process which does not require high reaction (arsine) pressures. It is another object of the invention to provide a process which does not require disposal of significant quantities of reactants and/or byproducts. It is still another object of the present invention to provide a process for the production of alkyl arsines which may be run in a continuous fashion.

SUMMARY OF THE INVENTION

The present invention is directed to the production of alkylarsines comprising contacting in the vapor phase an olefin and arsine over a Bronsted acid catalyst.

The present invention is further directed to the production of alkylarsines in a continuous manner.

The present invention is still further directed to the selective production of mono-alkylarsines relative to the total production of alkylarsines.

DESCRIPTION OF THE INVENTION INCLUDING PREFERRED EMBODIMENTS

Figure 1:
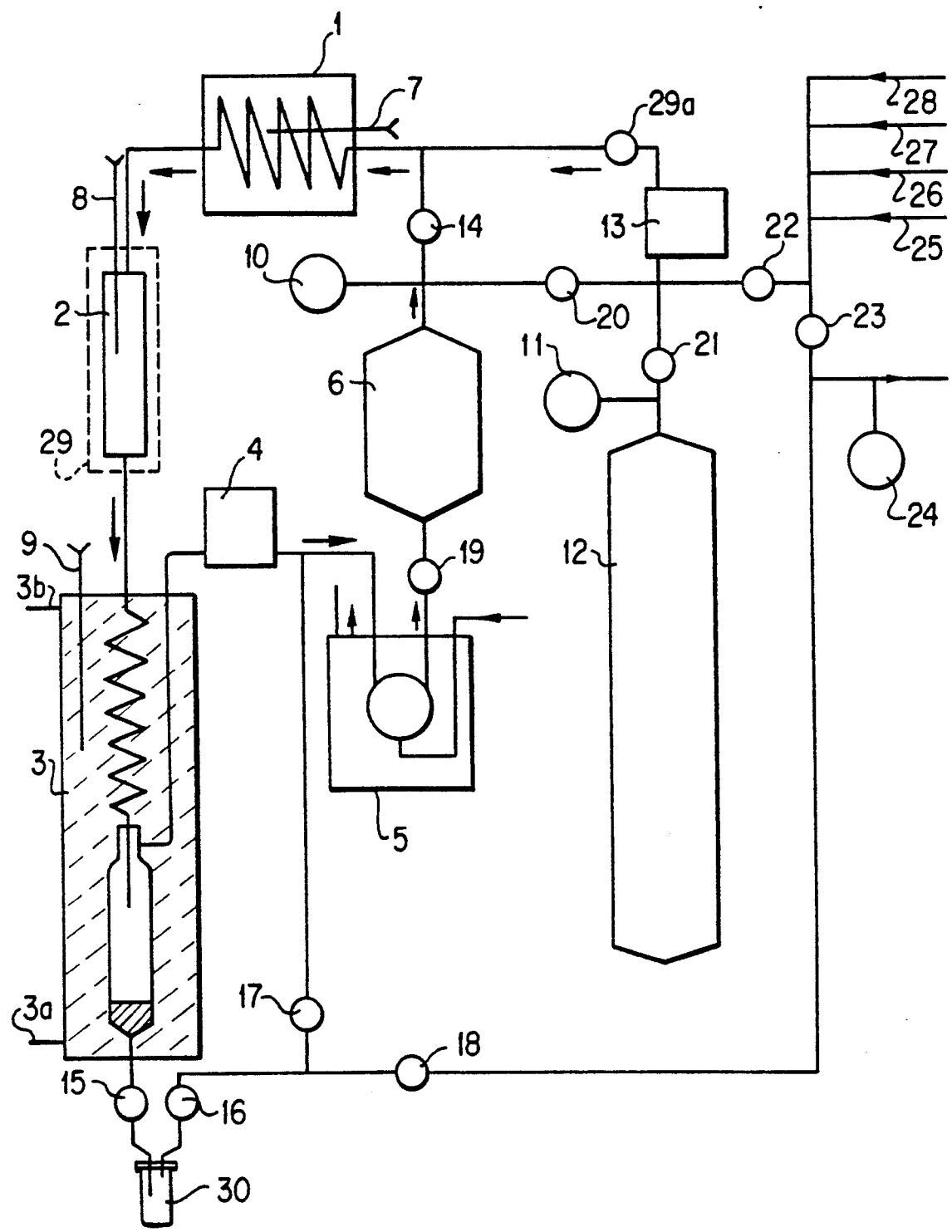
FIG. 1 is a schematic view of the microreactor used in Examples 1 and 2.

The term "olefin", as used herein, includes hydrocarbons having a single ethylenic double bond such as normal and branched chain aliphatic olefins, cycloaliphatic olefins, aryl substituted olefins and the like.

Any olefin which can be vaporized, caused to contact a Bronsted acid catalyst, and thereby be made to react with arsine to give alkylarsines, may be used in the present process.

Olefins containing preferably at least three carbon atoms are used in the present process. Olefins containing 3 to about 12 carbon atoms are more preferred, while olefins containing from 3 to about 6 carbon atoms are especially preferred.

Normal and branched chain aliphatic olefins preferred for making mono-alkylarsines according to the invention include, for example, propene, 1-butene, 2-butene, 2-methyl-1-propene, 2-methyl-1-butene, 2,3-dimethyl-1-butene, 2-ethyl-1-butene, 2-methyl-1-pentene, and the like. Mostly preferably, 2-methyl-1-propene is the olefin used in the practice of the present invention.

Cycloaliphatic olefins useful as olefin reactants in the invention include, for example, cyclopentene, cyclohexene, 2-methylcyclopentene, and the like.

The term "arsine", as used herein, means arsenic trihydride, $AsH_3$. The term "mono-alkylarsine", as used herein, means a compound of the formula $R^1AsH_2$, wherein $R^1$ is an alkyl or cycloalkyl moiety derived from one of the olefins listed above by Markonikov addition of $AsH_2$ to the olefin. The term "di-alkylarsine", as used herein, means a compound of the formula $R^1R^2AsH$, wherein $R^1$ is as before and $R^2$ is an alkyl moiety having seven carbons or less.

The catalyst used in the present process is a non-oxidizing strong Bronsted acid in a solid form. Suitable acids are those which protonate the olefin of interest, creating cationic intermediates which can be trapped by arsine or mono-alkylarsine.

The catalyst used in the present process may be a solid acid or a non-crystalline silicoaluminate, a heteropolyacid, or the like.

The catalyst used in the present process may also be a solid molecular Bronsted acid such as a polymeric acid derivative. Preferred polymer Bronsted acids include Amberlyst ® and Nafion ® and the like sold by Aldrich Chemical Co., Inc.

Alternatively, the catalyst used in the present process may comprise a non-oxidizing, strong, liquid, Bronsted acid, such as phosphoric acid, silicic acid, methanesulfonic acid, arsenic acid, or the like, absorbed onto a solid support. Examples of materials used to support such Bronsted acids for use in the present process include silica, mixed inorganic oxides, montmorillonite and the like.

Preferred catalysts are phosphoric acid, arsenic, and sulfonic acid. Especially preferred is phosphoric acid. As previously mentioned, the catalyst is present in a solid form. Liquid catalysts such as phosphoric acid are therefore preferably bound to a solid support, such as kieselguhr or silica gel. A suitable phosphoric acid catalyst is commercially available from UOP under the designation UOP-SPA. A suitable solid sulfonic acid catalyst is available from Alfa Inorganics Co. under the designation NAFIONH ®.

The catalyst is preferably present in a form which exposes maximum surface area to the reactants. Any suitable form of the acid, alone or on a support, may be used, including extrudates, flakes, pellets, powders, or particles of any shape. Use of catalyst in the form of extrudates is preferred. In the case of the preferred phosphoric acid catalyst, use of 8 to 18 mesh (V.S.) particles has been found to be especially efficient. Catalyst particles of this size have been found to cause only an acceptable pressure drop in the system, yet, they are of sufficient size to resist migration throughout the system.

If desired, pretreatment of the catalyst may be used to increase selectivity, reactivity, lifetime, and the like of solid catalysts used in the present process. For example, in use of the preferred UOP-SPA catalyst mentioned above, it has been found desirable to pretreat the catalyst bed by exposing it to the arsine-olefin mixture at temperatures for several hours about 80C.

The present process may be carried out in either a semi-batch or a continuous mode. It is preferred to carry out the present process in a continuous mode, especially when it is desired to obtain high purity monoalkylarsines, essentially free of dialkylarsine by-products.

When the present process is conducted in a semi-batch mode, provision should be made for catalyst placement and reactant gas agitation to insure that sufficient contact of gaseous reactants with catalyst occurs during accumulation of the liquid reaction products in the reaction vessel.

To conduct the present process in a continuous mode, an apparatus is required which comprises a reactor chamber containing a solid, Bronsted acid catalyst, with a means to pass a gaseous arsine-olefin mixture over the catalyst, and a means to collect alkylarsine products which are formed.

The type of reactor used to carry out the present process in continuous mode is not critical. Fixed fluidized, or ebulliated beds may be used.

Reaction temperatures in the range of 15° C. to about 220° C. may be used to carry out the present process in a batch or continuous mode. Preferred are temperatures from about 60° C. to about 195° C. Optimum reaction temperatures will depend on the olefin used, the type of catalyst, and the type of reactor. If desired, the catalyst bed may be heated to obtain improved selectivity, reactivity or other desirable reaction features. Heating may be accomplished by preheating of the reactants, by use of an auxiliary heater in the reaction vessel or both.

It is not necessary to use high arsine or olefin pressures in carrying out the present invention in a batch or continuous mode. It is only necessary to use pressures high enough to insure a sufficient flow of reactants over the catalyst using a continuous mode. Since high pressures of arsine are not required, it is not necessary to use compressed arsine gas in the practice of the current invention. Total pressures of arsine plus olefin of about 1 psig to about 25 psig are preferred, while pressures ranging from about 10 psig to about 20 psig are especially preferred. Use of total pressures higher than about 25 psig is possible but not necessary or desirable in the practice of invention.

In carrying out the present process in a batch or continuous mode, the amount of catalyst used and the residence time of arsine-olefin reagents in the reactor are not critical. Usually, it is desirable to adjust catalyst volumes and residence times to cause a clean, high, one-pass conversion of arsine - olefin to mono-alkylarsine when using a continuous mode.

When the present process is operated in a continuous mode, the method of collecting product is not critical. In a preferred collection mode, following contact with the catalyst, the alkylarsine-containing gas stream is cooled such that the high boiling alkylarsine products are condensed and thereby removed from the gas stream. Temperatures used in such condensation of product are not critical. It is desirable to use a collection temperature low enough to cause the condensation of mono-alkylarsine products, but not so low that reactant arsine and olefin are also condensed. When only monoalkylarsines are condensed, purification is simplified and, if desired, recycling arsine and olefin reactants is facilitated.

A preferred apparatus in which to conduct the present process in a continuous mode comprises a means to circulate an arsine olefin mixture of constant composition over a catalyst bed under conditions which cause olefin and arsine to combine to form alkylarsine, a means to condense alkylarsine which is formed from the mixtures of gases exiting the catalyst chamber, and a means to recycle the unreacted arsine-olefin mixture. It is preferred to arrange catalyst placement and circulation rate to insure all of the reactant gases make contact with the catalyst in one pass through the catalyst bed. It is further preferred to arrange the condensing system to condense as much of the alkylarsine product as possible, while not condensing the reactant arsine-olefin mixture. Recycling the unreacted arsine - olefin mixture in the way described above makes it possible to obtain high yields of desired mono-tertiary-butylarsine while minimizing formation of undesired di-tertiary-butyl-arsine and the need to dispose of unreacted arsine gas.

In an especially preferred continuous embodiment of the present invention, the apparatus shown in FIG. 1 is used. The apparatus contains a circulation loop comprising a preheater (1), heated reactor chamber (2), refrigerated condenser (3), mass-flow meter/controller (4), circulating pump (5), ballast (6), thermocouples (7), (8), and (9), and pressure gauge (10). The reactant feed system comprises a reservoir (12), pressure gauge (11), mass flow meter/controller (13), feed lines (25) for arsine, (26) for nitrogen, and (27) and (28) for olefins, a line to the vacuum pump (not shown in the Figure), and a vacuum gauge (24). The product reservoir (30) is connected to the condenser system through valves (16) and (18). Valves (21), (22), (23), (29), (14), (20), (19), and (17) are of the air actuated type. Product can be periodically or continuously transferred from the condenser (3) to the reservoir (30) through valve (15). The reactor (2) is first charged with catalyst and the entire system is evacuated through valve (23) in order to remove air. The pressure is monitored with vacuum gauge (24). If the preferred solid phosphoric acid catalyst is utilized, it is preconditioned as described above through its exposure to the reactant gas mixture, circulated using the pump (5), at low temperatures. After preconditioning of the catalyst bed, the preheated reaction gas mixture is introduced to the reactor (2) which is maintained at the process temperature by the reactor oven (29). The reactor exhaust, which contains the alkylarsine product, is then cooled in the condenser (3) in which product condenses and collects at the bottom thereof. The remaining reactant containing gas stream is pumped into the ballast (6) and, subsequently, back to the preheater (1). The pressure in the circulating loop is maintained at a constant level by the continuous injection of makeup reactant gas mixture from the ballast, through mass flow meter/controller (13), using valve (29a). The circulation rate in the loop is measured and regulated by the mass flow meter/controller (4). Either the reactant gas reservoir (12) or the reactor gas feed lines (25), (26), (27), or (28) can be used to provide the makeup reactant gas mixture.

In formation of mono-tertiary-butylarsine from arsine and 2-methyl-1-propene in the preferred continuous reaction mode and apparatus just described, it has been found that mixtures of mono- and di-tertiary-butylarsine are obtained in yields exceeding 90 wt. % based on consumed arsine and 90% based on consumed olefin. The mono- and di-tertiary-butylarsines are formed in mono- to di- ratios exceeding 10 and as high as 60. The mono- and di-tertiary-butylarsine mixtures which are obtained typically contain some dissolved 2-methyl-1-propene but only very low levels of germanium, sulfur, metallic, or oxidizing impurities, i.e. less than about 1 ppm. In the preferred continuous mode and apparatus, high mono-/di-tertiary-butylarsine ratios have been found to be favored by higher reactor bed temperatures and slower circulation rates within the apparatus. The mono-/di-ratio drops as catalyst nears the end of its useful life, approaching values characteristic of the prior art liquid phase process.

If desired, it is also possible to conduct the present process using a mono-alkylarsine and an olefin, both of which are capable of being transported in the vapor phase, as reagents, thereby forming a di-alkylarsine. Thus, reaction of mono-tertiary-butyl-arsine with 2-methyl-1-propene yields di-tertiary-butyl-arsine.

Mono-alkylarsines and especially mono-tertiary-butylarsine produced in accordance with the present invention can be used as a volatile source of arsenic in metalorganic chemical vapor deposition (MOCVD). The use of mono-tertiary-butylarsine in fabrication of semiconductors by MOCVD is disclosed in published European Patent Application No. 296,257.

A disclosure directed to the MOCVD process may be found in U.S. Pat. Nos. 4,368,098 and 4,404,265, the contents of which are expressly incorporated herein by reference. Semiconductor materials such as gallium arsenide (GaAs), fabricated by the MOCVD technique are typically found to be contaminated with electrically active elemental impurities such as germanium, silicon, carbon, and sulfur, which are derived from volatile impurities, containing the same elements, in the gaseous arsenic sources. For example, arsine gas is typically contaminated with difficult-to-predict levels of germanium, present as germane, $GeH_4$. High purity gaseous sources are thus required, especially gaseous sources which do not contain detrimental amounts of sulfur, germanium, metallic, and oxygenating impurities, all of which impurities adversely affect the electrical properties of semiconductor materials. A characteristic of mono-tertiary-butylarsine obtained by prior art procedures is that lengthy purification is required to obtain very high purity material which is suitable to prepare high quality gallium arsenide and related structures.

Mono-tertiary-butylarsine, for example, obtained by the process of the present invention using the preferred continuous mode described above, can be used without lengthy purification to fabricate high quality gallium arsenide thin films by MOCVD. This simplifies the preparation and increases the yield of gallium arsenide based on arsenic used.

If desired, mono-tertiary-butylarsine and other mono-alkylarsines obtained by the process of the present invention using the preferred continuous mode described above, can be even further purified by distillation. The method of distillation is not critical except that exposure to light and air should be avoided.

The following examples are set forth for purposes of illustration only and are not to be construed as limitations in the present invention except as set forth in the appended claims. All parts and percentages are by weight unless otherwise specified.

EXAMPLE 1

The apparatus shown in FIG. 1 is used. The raw materials used are VLSI grade arsine and CP grade 2-methyl-1-propene. The reactor is charged with 43 parts of UOPSPA-1 catalyst (8–18 mesh). The entire apparatus is evacuated for 1 hour at 0.01 psig and ambient temperature. The preheater, reactor and condenser are then pressured to 10 psig with arsine and the ballast is pressured to 15 psig with a 10/1 molar ratio of gas mixture of arsine/2-methyl-1-propene. With the condenser maintained at 4° C. and the slowly warming reactor at 49° C., the gas mixture in the ballast is circulated through the loop consisting of the preheater, reactor, condenser, pump, and ballast, at the rate of 5L/min. The pressure in the loop is maintained at 15 psig by the continuous addition of a 1/1 molar mixture of arsine/2-methyl-1-propene (reactant mixture). During the next 5 hours, the temperature of the reactor is gradually increased to 126° C. Following this catalyst conditioning procedure, the reactor temperature is increased to and maintained at 160°-164° C. while the reactant mixture is fed into the loop at a rate sufficient to maintain the pressure in the 15-17 psig range. After 2 hours of operation, the 82 parts of product collected are transferred to a stainless steel storage vessel. The ratio of mono-/di-tertiary-butyl arsines in the crude product is 46/1. The crude product is used in MOCVD growth of GaAs. There is obtained n-type GaAs having mobilities, on average, of 110,000 $cm^2$/V-sec.(77° K.)

EXAMPLE 2

The same apparatus and procedure for catalyst conditioning of Example 1 are used with a fresh 41 part charge of UOPSPA-1 (8-18 mesh). Following catalyst conditioning, the reactor is maintained at 157°-178° C. for 9.5 hours, with the condenser at 3° C., the circulation rate at 5L/min., and the feed rate of the 1/1 molar arsine/2-methyl-1-propene reactant mixture adjusted to be sufficient to maintain the pressure in the circulation loop in the 12-17 psig range. The resultant 450 parts of crude product are transferred to a stainless steel container. The ratio of mono-/di-tertiary-butylarsine in the crude product is approximately 11. The crude product obtained is combined with crude product from several similar reactions and purified by distillation. The mono-tertiary-butylarsine thereby obtained is used to grow GaAs thin films by MOCVD. The GaAs thereby obtained is n-type and has a mobility of 128,000 $cm^2$/V-sec.(77K).

EXAMPLE 3

Comparative Example

An autoclave is purged with nitrogen prior to introduction of nitrogen purged n-octane and 85% phosphoric acid in 1.4/1.0 volume ratio to a total volume of 40% of autoclave volume. VLSI grade arsine is then introduced to a pressure of 150 psig. The reactor is then heated to 95° C. with rapid stirring and additional arsine is added to give a measured total pressure of 400 psi. 2-Methyl-1-propene is then added under pressure, with additional arsine makeup and heating/cooling to maintain 95° C. and 325 psig or higher pressure over 3 hours. The autoclave is then allowed to cool to ambient temperature and vented to an arsine destroying means. Several purges with nitrogen are carried out, with venting to an arsine destroying means. The autoclave contents are then decanted under nitrogen atmosphere and acid and organic layers are separated. Acid layers are disposed of. Organic layers are washed with water and separated from the water, which is also disposed of. Crude product thus obtained comprises a mixture of octane, 2-methyl-1-propene, mono- and di-tertiary-butylarsine, with a mono- to di- ratio of approximately 3. Distillation of crude product through a 4 foot packed column is carried out to remove remaining arsine and 2-methyl-1-propene as lights, mono-tertiary-butylarsine as the main cut, and octane and di-tertiary-butylarsine as heavy fractions. The main cut from the first distillation is redistilled, to provide a 18% yield of mono-tertiary-butylarsine on arsine used. The mono-tertiary-butyl-arsine obtained in this procedure is used in chemical vapor deposition (MOCVD) to prepare an n-type gallium arsenide thin film having an average mobility of about 110,000 $cm^2$/V-sec.

EXAMPLE 4

Comparative Example

Alkylation of arsenic trichloride by tertiary-butyl magnesium chloride is carried out on 5L scale in a flask equipped with stirring means, thermometers, dropping funnel and an additional port with septum. Diethyl ether (3L) and arsenic trichloride (170 mL, 363 parts) are charged to the vessel which is then cooled below −70° C. 2N tertiary-butyl magnesium chloride in ether (1.05=L 1.05 mol Grignard/1.00 mole $AsCl_3$) is then added dropwise, maintaining the reaction temperature at −70° C. The mixture is stirred overnight at −70° C., then gradually allowed to warm to ambient temperature. Pentane (1.0L) is added and the mixture is stirred until a homogeneous appearing slurry is obtained. The mixture is filtered and the filter cake is washed with 0.5L of pentane. Distillation of the filtrate through a short column affords mono-tertiary-butylarsenic dichloride, b.p. 69° C. (25 mm), which solidifies to a white solid, 320 parts or 82% yield based on arsenic trichloride. Conversion of mono-tertiary-butylarsenic dichloride to mono-tertiary-butylarsine is carried out as follows. A 2L 3-neck vessel under nitrogen is charged first with tetraglyme (500 mL) and then, carefully, with lithium aluminum hydride (31 parts) at −77° C. A solution of mono-tertiary-butylarsenic dichloride (211 parts) in tetraglyme (450 mL) is then added by cannula with stirring over a period of one hour, at −77° C. Stirring is continued for 1.5 hours while the reaction mixture is allowed to warm to ambient temperature. Two short path distillations at ambient temperature and 20-50 microns pressure, provide 125 parts (90%) of crude mono-tertiary-butylarsine, 94% pure by gas chromatography. Distillation of this crude product using a 4-foot packed column affords approx. 70-80 parts of mono-tertiary-butylarsine of 98-99% purity by gas chromatography. Characteristic impurities include tertiary-butanol, tertiary-butyl chloride, secondary-butyl chloride, diethyl ether, 2-methylpentane, 2-methyl-1-propene, and n-pentane. The mono-tertiary-butylarsine obtained in this procedure is used in chemical vapor deposition (MOCVD) to prepare an n-type gallium arsenide thin film having a mobility less than 55,000 $cm^2$/V-sec., shown by standard methods of magnetophotoluminescence to contain characteristic germanium and sulfur impurities.

EXAMPLE 5

Figure 2:
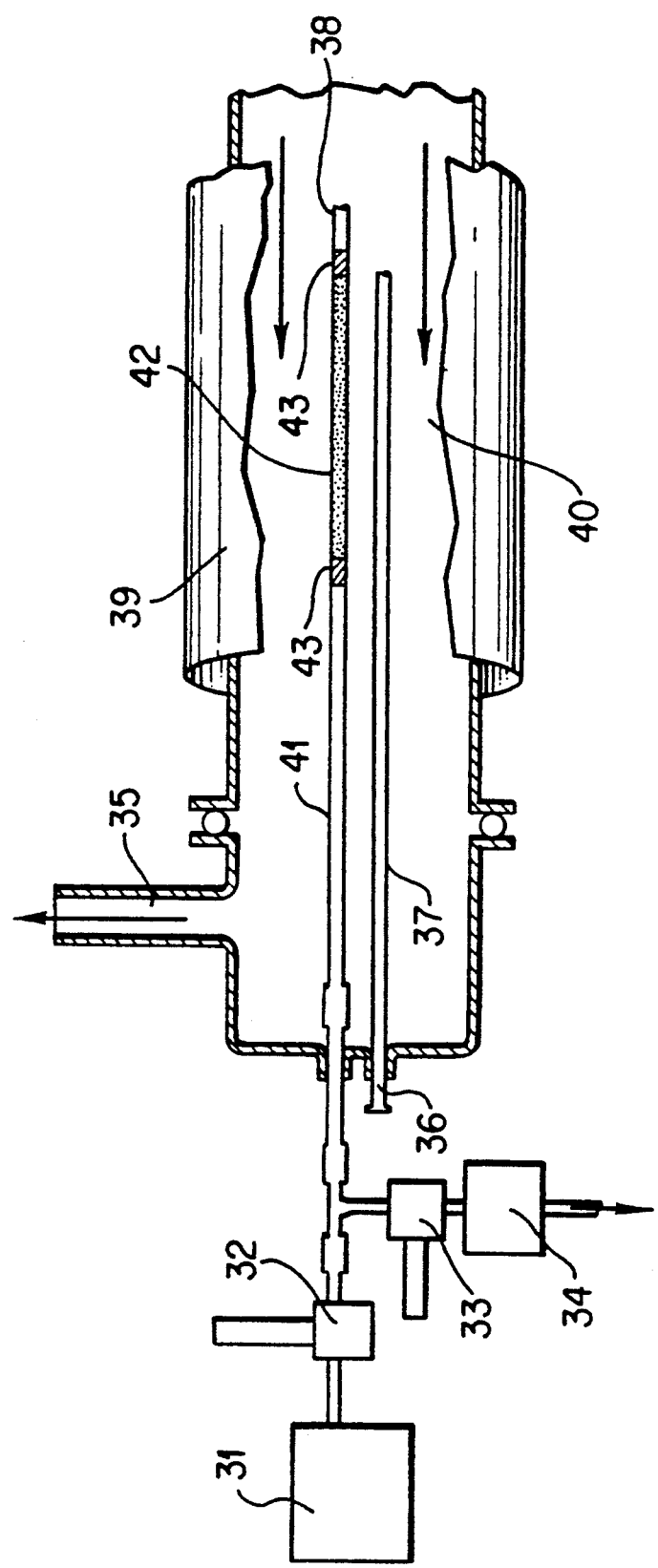
FIG. 2 is a schematic view of the apparatus used in the continuous operation of the claimed invention as in Examples 5, 6, and 7.

This example is carried out using the microreactor system shown in FIG. 2. The microreactor consists of a 16.5 cm section of a 0.6 cm OD×4.0 mm ID quartz tube (41) positioned in the center of a 4.0 cm OD×25. cm quartz tube (40), which is, in turn, positioned in the center of a microprocessor-controlled resistance-heated tube furnace (39). Tube (38) contains the catalyst (42) held in place by quartz wool plugs (43). It is heated with a microprocessor-controlled 2-zone resistance heater having electrical terminals and thermowell (37). Flow rates through the microprocessor (34) are regulated with a fine metering valve (33) located downstream of the reactor. Flow rates through the reactor are measured with a mass flow meter (not shown) also downstream of the reactor. A mixture of reactant gases (250 sccm) is injected into the large quartz tube through inlet (36). A fraction of the reactant gas flow is then allowed to pass through the microreactor by way of the tube inlet (38). The balance of reactant gases are exhausted through outlet (35). A fraction of the exhaust gas from the microreactor (about 0.3 sscm) is continuously injected into the mass spectrometer (31) through metering valve (32) for analysis of the composition thereof. Exhaust gases are not recirculated. Reactor pressures are maintained at either 200 or 400 Torr.

The catalyst charge is 1.94 parts of NafionH® NR-50, maintained at 110° C. and a total reactor pressure of 200 mm of hydrogen gas. The reactants charged are mono-tertiary-butyl arsine and 2-methyl-1-propene in 0.45 mol ratio and total partial pressure of approx. 15 mm. Formation of di-tertiary-butylarsine is detected in the reactor effluent by mass spectroscopy (parent peak at m/e=190).

EXAMPLE 6

The procedure of Example 4 is repeated using about 1.0 of AMBERLYST® 1010 solid sulfonic acid catalyst and 2.3 sccm stream of hydrogen containing mono-tertiary-butylarsine and 2-methyl-1-propene at partial pressures of 5 and 11 Torr, respectively. The reactor is maintained at about 22C. Ditertiarybutylarsine is detected in the exhaust gasses of the microreactor (parent peak at m/e 190).

EXAMPLE 7

The procedure of Example 4 is repeated except that the 1.5 parts of solid phosphoric acid catalyst UOP-SPA, maintained at 100C, are used and a 2.3 sccm stream of hydrogen gas containing arsine (0.4 mm partial pressure) and 2-methyl-1-propene (0.4 mm partial pressure) are charged to the reactor. Mono-tertiary-butylarsine (Parent ion at m/e 134) and 2-methyl-1-propene dimer (Parent ion at m/e 112) are detected in the reactor effluent by mass spectroscopy.

EXAMPLE 8-12

Following the procedure of Example 1, various olefins and acid catalysts are employed in replacement of those used therein. The olefins and catalysts employed are shown in Table I, below. In each instance, substantially identical results are achieved with regard to product yield and purity.

TABLE I

| Example | Olefin | Catalyst |
|---|---|---|
| 8 | 1-butene | Phosphoric Acid on Silica Gel |
| 9 | Cyclohexene | Silicoaluminate |
| 10 | 2,3-dimethyl-1-butene | Arsenic Acid on Montmorillonite |
| 11 | Propene | Silica Acid on Kieselguhr |
| 12 | 2-methyl-1-butene | Methane Sulfonic Acid on Silica Gel |

We claim:

1. A continuous process for the production of alkylarsines comprising continuously contacting, in the vapor phase, an olefin and arsine over a Bronsted acid catalyst.

2. A continuous process for the production of alkyl arsines comprising continuously contacting, in the vapor phase, an olefin and arsine over a Bronsted acid catalyst in a reaction vessel, condensing the resultant alkylarsine and removing the alkyl arsine so produced from said reaction vessel.

3. A process according to claim 2 wherein the alkyl arsine is mono-t-butylarsine.

4. The process of claim 2 wherein the olefin and arsine are recycled for a second pass over the catalyst.

5. The process of claim 4 wherein the alkyl arsine is t-butylarsine.

6. The process of claim 2 wherein said alkyl arsine is purified by distillation.

7. A process for the production of t-butylarsine comprising contacting, in the vapor phase, an olefin of four carbon atoms and arsine over a Bronsted acid catalyst.

* * * * *